United States Patent

Worthington et al.

Patent Number: 5,126,338
Date of Patent: Jun. 30, 1992

[54] FUNGICIDES WHICH ARE N-PYRIDYL-CYCLOPROPANE CARBOXAMIDES OR DERIVATIVES THEREOF

[75] Inventors: Paul A. Worthington, Maidenhead; Ian R. Matthews; David Bartholomew, both of Wokingham; Patrick J. Crowley, Crowthorne, all of England; Don R. Baker, Orinda; Karl J. Fisher, Petaluma, both of Calif.

[73] Assignee: Imperial Chemical Industries PLC, London, Great Britain

[21] Appl. No.: 638,294

[22] Filed: Jan. 3, 1991

[30] Foreign Application Priority Data

Jan. 4, 1990 [GB] United Kingdom ............... 9000130

[51] Int. Cl.$^5$ .................. A01N 43/40; C07D 213/75
[52] U.S. Cl. .................. 514/210; 514/212; 514/237.2; 514/318; 514/340; 514/341; 514/343; 514/344; 514/345; 514/346; 514/349; 514/352; 514/353; 544/124; 544/131; 546/194; 546/275; 546/276; 546/278; 546/279; 546/287; 546/289; 546/292; 546/297; 546/305; 546/306; 546/309; 546/310; 546/312
[58] Field of Search ............... 546/289, 292, 297, 305, 546/306, 287, 309, 312, 194, 275, 276, 278, 279, 310; 514/344, 346, 349, 352, 353, 210, 212, 237.2, 318, 340, 341, 343, 345; 544/124, 131

[56] References Cited

U.S. PATENT DOCUMENTS

| | | | |
|---|---|---|---|
| 4,766,134 | 8/1988 | Baker et al. | 514/346 |
| 4,766,135 | 8/1988 | Baker et al. | 514/346 |
| 4,767,771 | 8/1988 | Baker et al. | 514/346 |
| 4,767,772 | 8/1988 | Baker et al. | 514/346 |
| 4,797,407 | 1/1989 | Baker et al. | 514/346 |
| 4,800,205 | 1/1989 | Baker et al. | 514/346 |
| 4,808,600 | 2/1989 | Baker et al. | 514/346 |
| 4,824,854 | 4/1989 | Baker et al. | 514/346 |
| 4,831,044 | 5/1989 | Baker et al. | 514/346 |
| 4,845,107 | 7/1989 | Baker et al. | 514/346 |
| 4,894,379 | 1/1990 | Baker et al. | 514/332 |
| 4,895,858 | 1/1990 | Baker et al. | 514/352 |
| 4,914,115 | 4/1990 | Baker et al. | 514/346 |
| 4,931,451 | 6/1990 | Baker et al. | 514/330 |
| 4,975,442 | 12/1990 | Baker et al. | 514/346 |
| 4,975,443 | 12/1990 | Baker et al. | 514/332 |
| 4,977,164 | 12/1990 | Baker et al. | 514/318 |
| 4,992,503 | 2/1991 | Baker et al. | 514/346 |
| 5,019,565 | 5/1991 | Baker et al. | 546/22 |

Primary Examiner—Bernard Dentz
Attorney, Agent, or Firm—Michael J. Bradley

[57] ABSTRACT

Compounds of having the general formula (I):

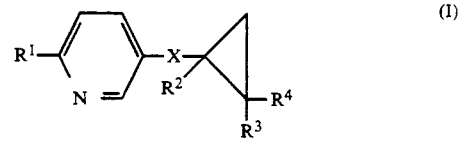

and stereoisomers thereof, wherein $R^1$ is hydrogen, halogen, $C_{1-4}$ alkoxy, $C_{1-4}$ alkyl, $C_{2-4}$ alkenyl, $C_{2-4}$ alkynyl, $C_{1-4}$ haloalkyl, $C_{1-4}$ haloalkoxy, COR or cyano; $R^2$, $R^3$ and $R^4$ are independently hydrogen, halogen or methyl, provided that $R^2$, $R^3$ and $R^4$ are not all hydrogen and provided that when one of them is methyl then at least one of the other two is not hydrogen;

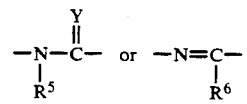

wherein $R^5$ is hydrogen, $C_{1-4}$ alkyl (optionally substituted by hydrogen or cyano), optionally substituted benzyl, $C_{2-4}$ alkenyl, $C_{2-4}$ alkynyl, cyano, COR, $C_{1-4}$ thioalkoxy, $C_{1-4}$ thiohaloalkoxy or $SNR^7R^8$; $R^7$ and $R^8$ are independently $C_{1-4}$ alkyl or $CO_2R$; Y is oxygen or sulphur; $R^6$ is $C_{1-4}$ alkoxy, $C_{1-4}$ thioalkoxy or $-NR^9R^{10}$; and $R^9$ and $R^{10}$ are independently hydrogen, $C_{1-4}$ alkyl, aryl or aralkyl or $R^9$ and $R^{10}$ join to form an optionally substituted heterocyclic ring and R is $C_{1-4}$ alkyl or $C_{3-7}$ cycloalkyl. These compounds are fungicidally active.

10 Claims, No Drawings

FUNGICIDES WHICH ARE N-PYRIDYL-CYCLOPROPANE CARBOXAMIDES OR DERIVATIVES THEREOF

The present invention relates to pyridyl cyclopropane derivatives that are useful as fungicides, to processes for preparing them, to fungicidal compositions containing them, and to methods of using them to combat fungi, especially fungal infections in plants.

According to the present invention there is provided a compound having the general formula (I):

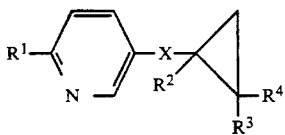

and stereoisomers thereof, wherein $R^1$ is hydrogen, halogen, $C_{1-4}$ alkoxy, $C_{1-4}$ alkyl, $C_{2-4}$ alkenyl, $C_{2-4}$ alkynyl, $C_{1-4}$ haloalkyl, $C_{1-4}$ haloalkoxy, COR or cyano; $R^2$, $R^3$ and $R^4$ are independently hydrogen, halogen or methyl, provided that $R^2$, $R^3$ and $R^4$ are not all hydrogen and provided that where one of then is methyl then at least one of the other two is not hydrogen;

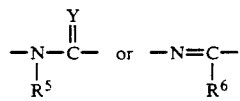

wherein $R^5$ is hydrogen, $C_{1-4}$ alkyl (optionally substituted by halogen or cyano), optionally substituted benzyl, $C_{2-4}$ alkenyl, $C_{2-4}$ alkynyl, cyano, COR, $C_{1-4}$ thioalkoxy, $C_{1-4}$ thiohaloalkoxy or $-SNR^7R^8$, wherein $R^7$ and $R^8$ are independently $C_{1-4}$ alkyl or $CO_2R$; Y is oxygen or sulphur; $R^6$ is $C_{1-4}$ alkoxy, $C_{1-4}$ thioalkoxy or $-NR^9R^{10}$; $R^9$ and $R^{10}$ are independently hydrogen, $C_{1-4}$ alkyl, aryl or aralkyl or $R^9$ and $R^{10}$ join to form an optionally substituted heterocyclic ring (for example, pyrrolidine, piperidine, morpholine, 1,2,4-triazole, imidazole, pyrazole); and R is $C_{1-4}$ alkyl or $C_{3-7}$ cycloalkyl.

The compounds of the invention can be obtained in the form of mixtures of geometric isomers of E and Z double bonds, these mixtures of isomers can be separated into individual isomers by methods in the art and such isomers constitute a part of the present invention.

Alkyl groups and the alkyl moieties of aralkyl, alkoxy and thioalkoxy contain from 1 to 4 carbon atoms and are either straight or branched chain groups, for example, methyl, ethyl, n-propyl, iso-propyl, n-butyl, iso-butyl, sec-butyl or tert-butyl.

Alkenyl groups contain from 2 to 4 carbon atoms and are alk-1-enyl, alk-2-enyl or alk-3-enyl, for example, vinyl, 2-prop-1-enyl, 1-prop-1-enyl, allyl, 2-but-2-enyl, 1-(2-methylprop-1-enyl), 1-but-1-enyl, 1-(1-methylprop-2-enyl), 1-(2-methylprop-2-enyl), 1-but-1-enyl, or 1-but-3-enyl.

Alkynyl groups contain from 2 to 4 carbon atoms and are, for example, ethynyl, prop-1-ynyl, propargyl or 2-but-3-ynyl.

Halogen includes fluorine, chlorine, bromine and iodine atoms.

Cycloalkyl groups contain from 3 to 7 carbon atoms and are, for example, cyclopropyl, cyclobutyl, cyclopentyl, cyclohexyl and cycloheptyl.

Haloalkyl groups and the haloalkyl moieties of haloalkoxy and thiohaloalkoxy contain from 1 to 4 carbon atoms and are, for example, halomethyl, haloethyl, halopropyl or halobutyl in which the halogen is fluorine, chlorine, bromine or iodine. For example the haloalkyl groups fluoromethyl, chloromethyl, fluoroethyl, chloroethyl, trifluoromethyl or trichloromethyl groups.

$R^9$ and $R^{10}$ together form an optionally substituted heterocyclic ring, preferably an 3 to 7-membered ring, for example, aziridine, azetidine, pyrrolidine, piperidine, hexamethyleneimine, morpholine, imidazole, pyrazole or 1,2,4-triazole, 1,2,3-triazole, pyrrole or tetrazole.

Aryl and the aryl moiety of aralkyl are preferably phenyl, and are optionally substituted with halogen, alkyl, haloalkyl, alkoxy, haloalkoxy, cyano, nitro, COR" or phenyl; and R" is hydrogen, hydroxy, $C_{1-4}$ alkyl or $C_{2-4}$ alkoxy.

Optional substituents on the phenyl moiety of benzyl are the same as those recited for aryl above.

In one aspect the present invention provides a compound having the general formula (I):

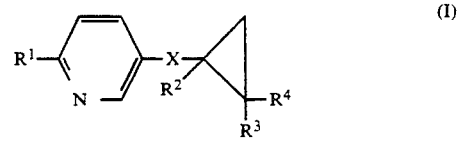

and stereoisomers thereof, wherein $R^1$ is hydrogen, halogen, $C_{1-4}$ alkoxy, $C_{1-4}$ alkyl, $C_{2-4}$ alkenyl, $C_{2-4}$ alkynyl, $C_{1-4}$ haloalkyl, $C_{1-4}$ haloalkoxy, COR or cyano; $R^2$, $R^3$ and $R^4$ are independently hydrogen or halogen provided that $R^2$, $R^3$ and $R^4$ are not all hydrogen;

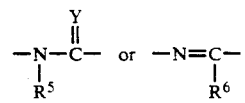

wherein $R^5$ is hydrogen, $C_{1-4}$ alkyl, optionally substituted benzyl, cyano, COR, $C_{1-4}$ thioalkoxy, $C_{1-4}$ thiohaloalkoxy or $-SNR^7R^8$, wherein $R^7$ and $R^8$ are independently $C_{1-4}$ alkyl or $CO_2R$; Y is oxygen or sulphur; $R^6$ is $C_{1-4}$ alkoxy, $C_{1-4}$ thioalkoxy or $-NR^9R^{10}$; $R^9$ and $R^{10}$ are independently hydrogen, $C_{1-4}$ alkyl, aryl or aralkyl or $R^9$ and $R^{10}$ join to form an optionally substituted heterocyclic ring (e.g. pyrrolidine, piperidine, morpholine, 1,2,4-triazole, imidazole, pyrazole); and R is $C_{1-4}$ alkyl or $C_{3-7}$ cycloalkyl.

In another aspect the present invention provides a compound having the general formula (I):

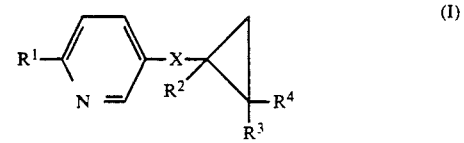

and stereoisomers thereof, wherein $R^1$ is hydrogen, fluorine, chlorine or $C_{1-4}$ alkoxy; $R^3$ and $R^4$ are independently hydrogen, methyl, chlorine, fluorine or bromine; $R^2$ is hydrogen or methyl, or, fluorine when $R^3$ is hydrogen or methyl and R⁴ is hydrogen, or, chlorine when R³ and R⁴ are both hydrogen, chlorine or methyl, or, bromine when R³ and R⁴ are both hydrogen; provided that R², R³ and R⁴ are not all hydrogen, and provided that when one of R², R³ or R⁴ is methyl then at least one of the other two is not hydrogen;

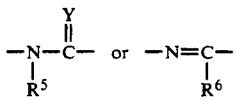

wherein R⁵ is hydrogen, C₁₋₄ alkyl (optionally substituted by halogen or cyano), optionally substituted benzyl, C₂₋₄ alkynyl or C₂₋₄ alkenyl; Y is oxygen or sulphur; R⁶ is C₁₋₄ alkoxy or —NR⁹R¹⁰; R⁹ and R¹⁰ are independently hydrogen, C₁₋₄ alkyl, aryl or aralkyl or R⁹ and R¹⁰ join to form an optionally substituted heterocyclic ring.

In a further aspect the present invention provides a compound having the general formula (I):

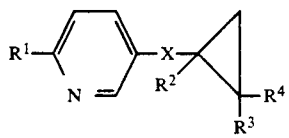

and stereoisomers thereof, wherein R¹ is fluorine, chlorine or C₁₋₄ alkoxy (especially methoxy); R³ and R⁴ are independently hydrogen, chlorine, fluorine or bromine; R² is hydrogen, or, fluorine, chlorine or bromine when R³ and R⁴ are both hydrogen, or, R², R³ and R⁴ are all chlorine; provided that R², R³, and R⁴ are not all hydrogen;

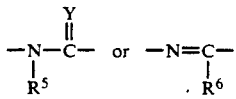

wherein R⁵ is hydrogen, C₁₋₄ alkyl (optionally substituted by halogen or cyano), optionally substituted benzyl, C₂₋₄ alkynyl (especially propargyl and but-2-ynyl) or C₂₋₄ alkenyl (especially allyl); Y is oxygen or sulphur; R⁶ is C₁₋₄ alkoxy or —NR¹⁰; R⁹ and R¹⁰ are independently hydrogen, C₁₋₄ alkyl, aryl or aralkyl or R⁹ and join to form an optionally substituted heterocyclic ring.

In a still further aspect the present invention provides a compound having the general formula (IX):

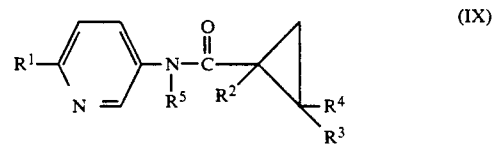

and stereoisomers thereof, wherein R¹ is fluorine, chlorine or methoxy; R² and R⁴ are both hydrogen and R³ is fluorine, or R² is hydrogen and R³ and R⁴ are both fluorine, or R² is fluorine and R³ and R⁴ are both hydrogen; R⁵ is hydrogen, C₁₋₄ alkyl (optionally substituted by cyano or fluorine), benzyl (wherein the phenyl moiety is optionally substituted by halogen, alkyl, haloalkyl, alkoxy, haloalkoxy, cyano or nitro), C₂₋₄ alkynyl (especially propargyl and but-2-ynyl) or C₂₋₄ alkenyl (especially allyl).

In another aspect the present invention provides a compound having the general formula (IX):

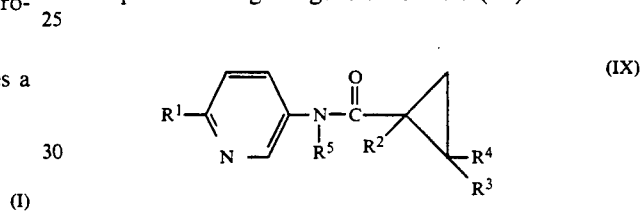

and stereoisomers thereof, wherein R¹ is methoxy; R² and R⁴ are both hydrogen and R³ is fluorine, or R² is hydrogen and R³ and R⁴ are both fluorine, or R² is fluorine and R³ and R⁴ are both hydrogen; R⁵ is hydrogen, C₁₋₂ alkyl (optionally substituted by cyano or fluorine), benzyl (wherein the phenyl moiety is optionally substituted by halogen, alkyl, haloalkyl, alkoxy, haloalkoxy, cyano or nitro), propargyl, allyl or but-2-ynyl.

In a further aspect the invention provides a compound having the formula (XV):

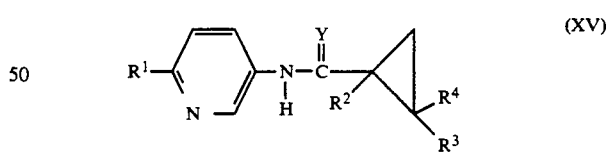

and stereoisomers thereof; wherein R¹ is C₁₋₄ alkoxy (especially methoxy) or halogen (especially fluorine); Y is oxygen or sulphur and R², R³ and R⁴ are hydrogen or fluorine provided that they are not all hydrogen.

Examples of compounds of the invention of formula (I) are given in Table I where X is

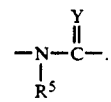

TABLE I

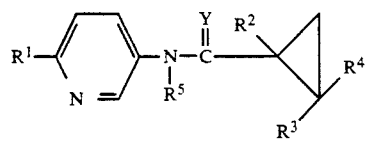

| Compound No | R¹ | R² | R³ | R⁴ | R⁵ | Y | mp °C. | Comments |
|---|---|---|---|---|---|---|---|---|
| 1 | CH₃O | F | H | H | H | O | 121–122 | |
| 2 | CH₃O | F | H | H | H | S | | |
| 3 | F | F | H | H | H | O | 108–111 | |
| 4 | F | F | H | H | H | S | | |
| 5 | CH₃O | H | F | F | H | O | 122–123 | |
| 6 | CH₃O | H | F | F | H | S | | |
| 7 | F | H | F | F | H | O | 108–110 | |
| 8 | F | H | F | F | H | S | | |
| 9 | Cl | F | H | H | H | O | 108 | |
| 10 | CH₃O | Br | H | H | H | O | 79–80 | |
| 11 | F | Br | H | H | H | O | 92–95 | |
| 12 | Cl | Br | H | H | H | O | 120–122 | |
| 13 | CH₃O | Cl | H | H | H | O | | |
| 14 | F | Cl | H | H | H | O | | |
| 15 | Cl | Cl | H | H | H | O | | |
| 16 | Cl | H | F | F | H | O | 157–159 | |
| 17 | OCH₃ | H | F | H | H | O | 119–120 | RR:SS 1:1 |
| 18 | OCH₃ | H | F | H | H | O | 133–134 | RS:SR 1:1 |
| 19 | F | H | F | H | H | O | | cis |
| 20 | Cl | H | F | H | H | O | | cis |
| 21 | F | H | F | H | H | O | | trans |
| 22 | Cl | H | F | H | H | O | | trans |
| 23 | OCH₃ | CH₃ | F | F | H | O | 85–86 | |
| 24 | F | CH₃ | F | F | H | O | 108–110 | |
| 25 | Cl | CH₃ | F | F | H | O | oil | |
| 26 | OCH₃ | H | F | Cl | H | O | 81.0–83.5 | all 4 diastereomers |
| 27 | Cl | H | F | Cl | H | O | | |
| 28 | F | H | F | Cl | H | O | 73–76 | all 4 diastereomers |
| 29 | OCH₃ | CH₃ | F | Cl | H | O | gum | all 4 diastereomers |
| 30 | F | CH₃ | F | Cl | H | O | 118–119 | all 4 diastereomers |
| 31 | Cl | CH₃ | F | Cl | H | O | 95–97 | all 4 diastereomers |
| 32 | OCH₃ | CH₃ | Cl | Cl | H | O | 144–145 | |
| 33 | F | CH₃ | Cl | Cl | H | O | 136–137 | |
| 34 | Cl | CH₃ | Cl | Cl | H | O | 128–129 | |
| 35 | OCH₃ | F | H | H | CH₃ | O | oil | |
| 36 | Cl | F | H | H | CH₃ | O | | |
| 37 | F | F | H | H | CH₃ | O | | |
| 38 | OCH₃ | F | H | H | CH₂C≡CH | O | oil | |
| 39 | Cl | F | H | H | CH₂C≡CH | O | | |
| 40 | F | F | H | H | CH₂C≡CH | O | | |
| 41 | OCH₃ | F | H | H | CH₂CH=CH₂ | O | oil | |
| 42 | Cl | F | H | H | CH₂CH=CH₂ | O | | |
| 43 | F | F | H | H | CH₂CH=CH₂ | O | | |
| 44 | OCH₃ | F | H | H | CH₂C₆H₅ | O | oil | |
| 45 | Cl | F | H | H | CH₂C₆H₅ | O | | |
| 46 | F | F | H | H | CH₂C₆H₅ | O | | |
| 47 | OCH₃ | F | H | H | CH₂C≡CCH₃ | O | 85–87 | |
| 48 | Cl | F | H | H | CH₂C≡CCH₃ | O | | |
| 49 | F | F | H | H | CH₂C≡CCH₃ | O | | |
| 50 | OCH₃ | F | H | H | CH₂CN | O | | |
| 51 | OCH₃ | F | H | H | CH₂F | O | | |
| 52 | OCH₃ | F | H | H | CHF₂ | O | | |
| 53 | OCH₃ | F | H | H | CH₂cyclopropyl | O | | |
| 54 | Cl | F | H | H | CH₂CN | O | | |
| 55 | F | F | H | H | CH₂CN | O | | |
| 56 | Cl | F | H | H | CH₂F | O | | |
| 57 | F | F | H | H | CH₂F | O | | |
| 58 | Cl | F | H | H | CHF₂ | O | | |
| 59 | F | F | H | H | CHF₂ | O | | |
| 60 | Cl | F | H | H | CH₂cyclopropyl | O | | |
| 61 | F | F | H | H | CH₂cyclopropyl | O | | |
| 62 | OCH₃ | F | CH₃ | H | CH₃ | O | | |
| 63 | OCH₃ | F | CH₃ | H | CH₂CH=CH₂ | O | | |
| 64 | OCH₃ | F | CH₃ | H | CH₂C≡CH | O | | |
| 65 | OCH₃ | F | CH₃ | H | CH₂C≡CCH₃ | O | | |
| 66 | OCH₃ | F | CH₃ | H | CH₂CN | O | | |
| 67 | OCH₃ | F | CH₃ | H | CH₂F | O | | |
| 68 | OCH₃ | F | CH₃ | H | CHF₂ | O | | |
| 69 | OCH₃ | F | CH₃ | H | CH₂cyclopropyl | O | | |
| 70 | Cl | F | CH₃ | H | CH₃ | O | | |
| 71 | Cl | F | CH₃ | H | CH₂CH=CH₂ | O | | |
| 72 | Cl | F | CH₃ | H | CH₂C≡CH | O | | |

TABLE I-continued

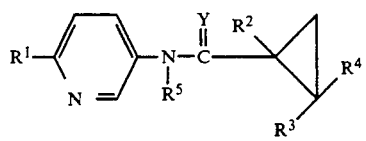

| Compound No | $R^1$ | $R^2$ | $R^3$ | $R^4$ | $R^5$ | Y | mp °C. | Comments |
|---|---|---|---|---|---|---|---|---|
| 73 | Cl | F | CH₃ | H | CH₂C≡CCH₃ | O | | |
| 74 | Cl | F | CH₃ | H | CH₂CN | O | | |
| 75 | Cl | F | CH₃ | H | CH₂F | O | | |
| 76 | Cl | F | CH₃ | H | CHF₂ | O | | |
| 77 | Cl | F | CH₃ | H | CH₂cyclopropyl | O | | |
| 78 | F | F | CH₃ | H | CH₃ | O | | |
| 79 | F | F | CH₃ | H | CH₂CH=CH₂ | O | | |
| 80 | F | F | CH₃ | H | CH₂C≡CH | O | | |
| 81 | F | F | CH₃ | H | CH₂C≡CCH₃ | O | | |
| 82 | F | F | CH₃ | H | CH₂CN | O | | |
| 83 | F | F | CH₃ | H | CH₂F | O | | |
| 84 | F | F | CH₃ | H | CHF₂ | O | | |
| 85 | F | F | CH₃ | H | CH₂cyclopropyl | O | | |
| 86 | OCH₃ | H | F | F | CH₂C₆H₅ | O | | |
| 87 | OCH₃ | H | F | H | CH₂C₆H₅ | O | | |
| 88 | OCH₃ | H | F | F | CH₃ | O | | |
| 89 | Cl | H | F | F | CH₃ | O | | |
| 90 | F | H | F | F | CH₃ | O | | |
| 91 | OCH₃ | H | F | F | CH₂CH=CH₂ | O | | |
| 92 | Cl | H | F | F | CH₂CH=CH₂ | O | | |
| 93 | F | H | F | F | CH₂CH=CH₂ | O | | |
| 94 | OCH₃ | H | F | F | CH₂C≡CH | O | | |
| 95 | Cl | H | F | F | CH₂C≡CH | O | | |
| 96 | F | H | F | F | CH₂C≡CH | O | | |
| 97 | OCH₃ | H | F | F | CH₂C≡CCH₃ | O | | |
| 98 | Cl | H | F | F | CH₂C≡CCH₃ | O | | |
| 99 | F | H | F | F | CH₂C≡CCH₃ | O | | |
| 100 | OCH₃ | H | F | F | CH₂CN | O | | |
| 101 | Cl | H | F | F | CH₂CN | O | | |
| 102 | F | H | F | F | CH₂CN | O | | |
| 103 | OCH₃ | H | F | F | CH₂F | O | | |
| 104 | Cl | H | F | F | CH₂F | O | | |
| 105 | F | H | F | F | CH₂F | O | | |
| 106 | OCH₃ | H | F | F | CHF₂ | O | | |
| 107 | Cl | H | F | F | CHF₂ | O | | |
| 108 | F | H | F | F | CHF₂ | O | | |
| 109 | OCH₃ | H | F | F | CH₂cyclopropyl | O | | |
| 110 | Cl | H | F | F | CH₂cyclopropyl | O | | |
| 111 | F | H | F | F | CH₂cyclopropyl | O | | |
| 112 | OCH₃ | H | Cl | H | CH₃ | O | | |
| 113 | Cl | H | Cl | H | CH₃ | O | | |
| 114 | F | H | Cl | H | CH₃ | O | | |
| 115 | OCH₃ | H | Cl | H | H | O | | |
| 116 | Cl | H | Cl | H | H | O | | |
| 117 | F | H | Cl | H | H | O | | |
| 118 | OCH₃ | Cl | CH₃ | CH₃ | H | O | | |
| 119 | Cl | Cl | CH₃ | CH₃ | H | O | | |
| 120 | F | Cl | CH₃ | CH₃ | H | O | | |
| 121 | OCH₃ | Cl | Cl | Cl | H | O | | |
| 122 | Cl | Cl | Cl | Cl | H | O | | |
| 123 | F | Cl | Cl | Cl | H | O | | |
| 124 | OCH₃ | H | Cl | Cl | H | O | | |
| 125 | Cl | H | Cl | Cl | H | O | | |
| 126 | F | H | Cl | Cl | H | O | | |
| 127 | OCH₃ | CH₃ | Cl | H | H | O | | |
| 128 | Cl | CH₃ | Cl | H | H | O | | |
| 129 | F | CH₃ | Cl | H | H | O | | |
| 130 | OCH₃ | CH₃ | Cl | Cl | H | O | | |
| 131 | Cl | CH₃ | Cl | Cl | H | O | | |
| 132 | F | CH₃ | Cl | Cl | H | O. | | |

TABLE II

SELECTED PROTON NMR DATA

Table II shows selected proton nmr data for certain compounds described in Table I. Chemical shifts are measured in ppm from tetramethylsilane, and deuterochloroform was used as solvent throughout.

| Compound No | NMR Data |
|---|---|
| 1 | 1.36(c,2H); 1.46(c,2H); 3.91(s,3H); 6.75(d,1H); 7.93(dd,1H); 8.00(br.s,1H); 8.23(d,1H). |
| 3 | 1.40–1.54(c,4H); 6.95(dd,1H); 8.15(br.s,1H); 8.23(c,1H); 8.30(s,1H). |
| 5 | 1.80(c,1H); 2.22(c,1H); 2.41(c,1H); 3.91(s,3H); 6.73(d,1H); 7.20(br.s,1H); 7.90(dd,1H); 8.15(d,1H). |
| 7 | 1.82(c,1H); 2.24(c,1H); 2.45(c,1H); 6.95(dd,1H); 7.54(br.s,1H); 8.11(c,2H). |
| 10 | 1.42(c,2H); 1.81(c,2H); 3.94(s,3H); 6.75(d,1H); 7.85(dd,1H); 8.20(d,1H); 8.43(br.s,1H). |
| 11 | 1.47(c,2H); 1.82(c,2H); 6.94(dd,1H); 8.15(c,1H); 8.25(s,1H); 8.60(br.s,1H). |
| 12 | 1.46(c,2H); 1.83(c,2H); 7.33(d,1H); 8.09(dd,1H); 8.45(d,1H); 8.60(br.s,1H). |
| 16 | 1.84(c,1H); 2.25(c,1H); 2.45(c,1H); 7.32(d,1H); 7.43(br.s,1H); 8.15(dd,1H); 8.39(d,1H). |
| 17 | 1.25(c,1H); 1.75–1.90(c,2H); 3.91(s,3H); 4.84(dc,1H); 6.74(d,1H); 7.25(s,1H); 7.95(dd,1H); 8.15(d,1H). |
| 18 | 1.40–1.55(c,2H); 1.90–2.06(c,1H); 3.92(s,3H); 4.89(dc,1H); 6.73(d,1H); 7.30(br.s,1H); 7.87(dd,1H); 8.14(d,1H). |
| 23 | 1.39(c,1H); 1.60(s,3H); 2.25(c,1H); 3.91(s,3H); 6.75(d,1H); 7.31(br.s,1H); 7.87(dd,1H); 8.15(d,1H). |
| 24 | 1.43(c,1H); 1.60(s,3H); 2.27(c,1H); 6.95(dd,1H); 7.43(br.s,1H); 8.15–8.22(c,2H). |
| 25 | 1.42(c,1H); 1.61(s,3H); 2.25(c,1H); 7.31(d,1H); 7.48(br.s,1H); 8.14(dd,1H); 8.40(d,1H). |
| 26 | 1.87–2.60(c,3H); 3.92(s,3H); 6.75(d,1H); 7.32(br.s,1H); 7.93(dd,1H); 8.18(d,1H). |
| 28 | 1.90–2.60(c,3H); 6.95(dd,1H); 7.55(br.s,1H); 8.24(c,2H). |
| 29 | 1.45–1.60(c,1H); 1.65(c,3H); 2.10–2.45(c,1H); 3.91(s,3H); 6.74(d,1H); 7.30(br.s,1H); 7.88(dd,1H); 8.17(d,1H). |
| 30 | 1.31(m4); 1.50–1.60(m4); 1.65(c); 2.15(m4); 2.42(m4); 6.95(c); 7.53(br.s); 8.14–8.25(c). (4 Diastereomers). |
| 31 | 1.30 (m4); 1.55(m4); 1.65(c); 2.13(m4); 2.41(m4); 7.30; 7.33(d); 7.82(br.s); 7.88(br.s); 8.11(d); 8.16(d); 8.40(c). (4 Diastreomers). |
| 32 | 1.48(d,1H); 1.73(s,3H); 2.30(d,1H); 3.92(s,3H); 6.75(d,1H); 7.35(br.s,1H); 7.87(dd,1H); 8.19(d,1H). |
| 33 | 1.52(d,1H); 1.76(s,3H); 2.33(d,1H); 6.95(dd,1H); 7.45(br.s,1H); 8.18(c,1H); 8.25(c,1H). |
| 34 | 1.51(d,1H); 1.74(s,3H); 2.32(d,1H); 7.33(d,1H); 7.47(br.s,1H); 8.14(dd,1H); 8.43(d,1H). |
| 35 | 1.05–1.20(c,2H); 1.38–1.46(c,2H); 1.57(s,3H); 3.95(s,3H); 6.78(d,1H); 7.49(dd,1H); 8.06(d,1H). |
| 38 | 1.09–1.20(c,3H); 1.40–1.48(c,2H); 2.25(c,1H); 3.95(s,3H); 4.45(c,2H); 6.80(d,1H); 7.55(dd,1H); 8.13(d,1H). |
| 41 | 1.05–1.20(c,2H); 1.35–1.45(c,2H); 3.94(s,3H); 4.30(d,2H); 5.15(dd,2H); 5.77–5.94(c,1H); 6.74(d,1H); 7.43(dd,1H); 8.01(d,1H). |
| 44 | 0.95–1.40(c,4H); 3.80(s,3H); 4.90(s,2H); 6.60(d,1H); 7.00–7.20(c,6H); 7.75(d,1H). |
| 47 | 0.90–1.50(c,4H); 1.75(s,3H); 3.90(s,3H); 4.35(d,2H); 6.75(d,1H); 7.50(dd,1H); |

TABLE II-continued

SELECTED PROTON NMR DATA

Table II shows selected proton nmr data for certain compounds described in Table I. Chemical shifts are measured in ppm from tetramethylsilane, and deuterochloroform was used as solvent throughout.

| Compound No | NMR Data |
|---|---|
| | 8.05(d,1H). |

The following abbreviations are used:
s—singlet
d—doublet
c—complex
dc—doublet of complex signals
br.s—broad singlet
m4—quartet Compounds of general formula (I) wherein the X group is

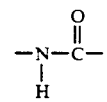

are compounds of general formula (II):

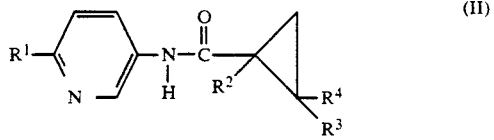

wherein $R^1$, $R^2$, $R^3$ and $R^4$ are as defined above, can be prepared by coupling an amine of general formula (III):

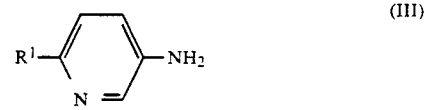

wherein $R^1$ is defined above, with a carboxylic acid of general formula (IV):

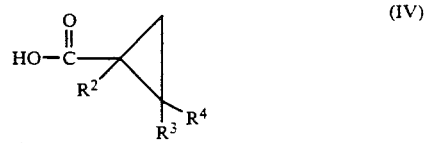

wherein $R^2$, $R^3$ and $R^4$ are as defined above, by methods set out in the literature. The coupling is usually achieved by using 1,3-dicyclohexylcarbodiimide (DCC) or 1-ethyl-3-(3-dimethylaminopropyl) carbodiimide hydrochloride.

An alternative process involves converting the acid (IV) to an acid chloride of formula (V) or an acid imidazole of formula (VI):

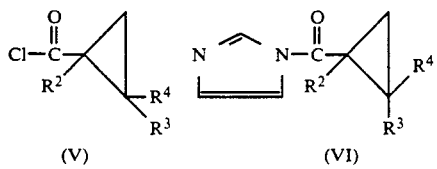

followed by reaction of these intermediates with the amine (III).

The acid chlorides (V) are prepared by reacting the carboxylic acids (IV) with thionyl chloride or oxalyl chloride in an inert solvent such as methylene chloride. The acid imidazoles (VI) can be prepared by treating the carboxylic acids (IV) with carbonyl di-imidazole in an inert solvent such as methylene chloride.

The amines of general formula (III) can be prepared by methods set out in the literature. The carboxylic acids of general formula (IV) can be prepared by reacting a methyl ketone of general formula (VII):

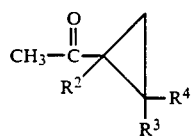

wherein $R^2$, $R^3$ and $R^4$ are as defined above, with a suitable oxidising agent (for example sodium hypobromite).

The methyl ketones (VII) are prepared by methods set out in the literature. (See for example, Lutz Fitjer, Synthesis 1977 p. 189).

Thioamide compounds of general formula (VIII) where the X group of the compound of general formula (I) is

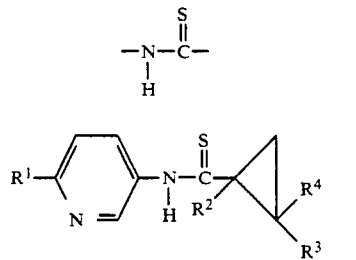

can be prepared by treating the amides of general formula (II) with a suitable sulphurating reagent, such as phosphorus pentasulphide, Lawesson's reagent or Belleau's reagent in a convenient solvent (such as toluene or dichloromethane).

Compounds of general formula (IX) where the X group of a compound of general formula (I) is

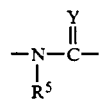

(the $R^5$ group being other than hydrogen) and Y is oxygen, can be prepared (as shown in Scheme 1 below) by treating an amide of general formula (II) with an alkylating agent of general formula (XI), where L is a halogen atom or another good leaving group, and a base (such as potassium hydroxide or sodium hydride) in a suitable solvent (such as dimethyl sulphoxide or dimethylformamide).

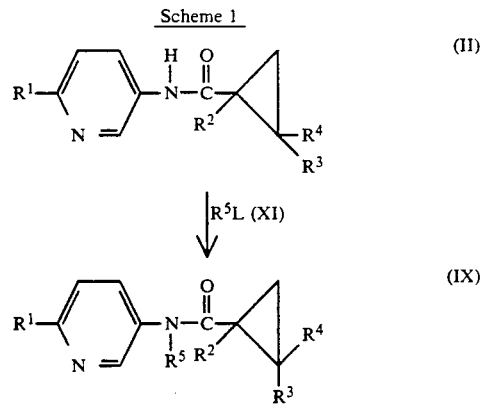

Compounds of general formula (XV) where the X group of a compound of general formula (I) is

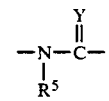

wherein the $R^5$ group is other than hydrogen and Y is sulphur, can be prepared (as shown in Scheme 2 below) by treating amides of general formula (IX) with a suitable sulphurating reagent, such as phosphorus pentasulphide, Lawesson's reagent or Belleau's reagent, in a convenient solvent (such as toluene or dichloromethane).

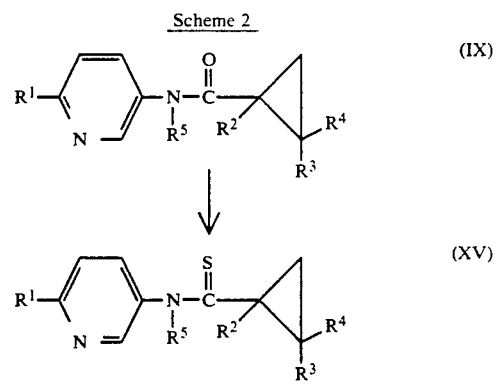

Compounds of general formula (XII) where the X group of a compound of general formula (I) is —N=C($R^6$)— and the $R^6$ group is as defined above, can be prepared (as shown in Scheme 3 below) by treating an amide of general formula (II) with imidoylating reagents such as phosphorus pentachloride, phosphorus pentabromide or carbon tetrachloride and triphenylphosphine to give an imidoyl halide (XIII) intermediate wherein M is a halogen. The imidoyl halide (XIII) is then reacted with a compound $R^6H$ (XIV) in the presence of a convenient base (such as triethylamine, or sodium hydride) in a convenient solvent (such as tetrahydrofuran or dichloromethane).

Scheme 3

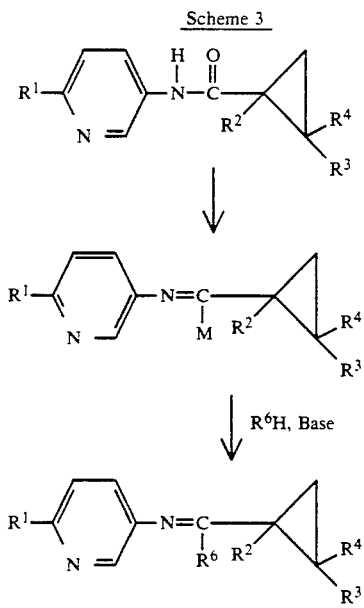

The carboxylic acids of general formula (IV) are known in the literature or they can be prepared by hydrolysis of their esters, which are known in the literature, using methods set out in the literature.

Carboxylic acids of general formula (XVI):

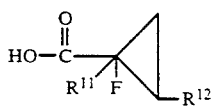

wherein $R^{11}$ is hydrogen or methyl, and $R^{12}$ is fluorine or chlorine can be prepared either as shown in Scheme 4 below, or by suitable adaptation of methods in EP-A2-0351647 and EP-A2-0351650.

Scheme 4

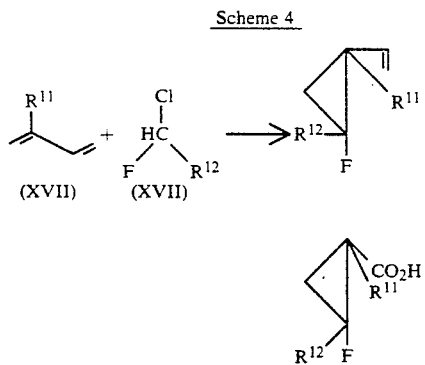

Thus, reacting a butadiene of general formula (XVII) with a compound of general formula (XVIII) in the presence of 1-chloro-2,3-epoxypropane (epichlorohydrin) at a suitable temperature gives a compound of general formula (XIX). Oxidising the compound of general formula (XIX) under suitable conditions (for example, using potassium permanganate) gives a carboxylic acid of general formula (XVI).

In other aspects of the invention there are provided processes, as hereinbefore described, for preparing the compounds of the invention, and the claimed intermediates, 1-fluorocyclopropane carboxylic acid and the acid chloride, imidazole derivative, salts and esters thereof.

The compounds of the invention are active fungicides and may be used to control one or more of the following pathogens:

*Pyricularia oryzae* on rice. *Puccinia recondita, Puccinia striiformis* and other rusts on wheat, *Puccinia hordei, Puccinia striiformis* and other rusts on barley, and rusts on other hosts e.g. coffee, pears, apples, peanuts, vegetables and ornamental plants. *Erysiphe graminis* (powdery mildew) on barley and wheat and other powdery mildews on various hosts such as *Sphaerotheca macularis* on hops, *Sphaerotheca fuliginea* on cucurbits (e.g. cucumber), *Podosphaera leucotricha* on apple and *Uncinula necator* on vines. *Helminthosporium* spp., *Rhynchosporium* spp., *Septoria* spp., *Pyrenophora* spp., *Pseudocercosporella herpotrichoides* and *Gaeumannomyces graminis* on cereals. *Cercospora arachidicola and Cercosporidium personata* on peanuts and other *Cercospora* species on other hosts, for example, sugar beet, bananas, soya beans and rice. *Botrytis cinerea* (grey mould) on tomatoes, strawberries, vegetables, vines and other hosts. *Alternaria* spp. on vegetables (e.g. cucumber), oil-seed rape, apples, tomatoes and other hosts. *Venturia inaequalis* (scab) on apples. *Plasmopara viticola* on vines. Other downy mildews such as *Bremia lactucae* on lettuce, *Peronospora* spp. on soybeans, tobacco, onions and other hosts, *Pseudoperonospora humuli* on hops and *Pseudoperonospora cubensis* on cucurbits. *Phytophthora infestans* on potatoes and tomatoes and other *Phytophthora* spp. on vegetables, strawberries, avocado, pepper, ornamentals, tobacco, cocoa and other hosts. *Thanatephorus cucumeris* on rice and other *Rhizoctonia* species on various hosts such as wheat and barley, vegetables, cotton and turf.

Some of the compounds show a broad range of activities against fungi in vitro. They may also have activity against various post-harvest diseases of fruit (e.g. *Penicillium digitatum* and *italicum* and *Trichoderma viride* on oranges, *Gloeosporium musarum* on bananas and *Botrytis cinerea* on grapes).

Further, some of the compounds may be active as seed dressings against pathogens including *Fusarium* spp., *Septoria* spp., *Tilletia* spp., (bunt, a seed-borne disease of wheat), *Ustilago* spp. and *Helminthosporium* spp. on cereals, *Rhizoctonia solani* on cotton and *Pyricularia oryzae* on rice.

The compounds may move acropetally/locally in plant tissue. Moreover, the compounds may be volatile enough to be active in the vapour phase against fungi on the plant.

The invention therefore provides a method of combating fungi which comprises applying to a plant, to a seed of a plant or to the locus of the plant or seed a fungicidally effective amount of a compound as hereinbefore defined, or a composition containing the same.

The compounds may be used directly for agricultural purposes but are more conveniently formulated into compositions using a carrier or diluent. The invention thus provides fungicidal compositions comprising a compound as hereinbefore defined and an acceptable carrier or diluent therefor.

The compounds can be applied in a number of ways. For example, they can be applied, formulated or unformulated, directly to the foliage of a plant, to seeds or to other medium in which plants are growing or are to be planted, or they can be sprayed on, dusted on or applied as a cream or paste formulation, or they can be applied as a vapour or as slow release granules.

Application can be to any part of the plant including the foliage, stems, branches or roots, or to soil surrounding the roots, or to the seed before it is planted, or to the soil generally, to paddy water or to hydroponic culture systems. The invention compounds may also be injected into plants or sprayed onto vegetation using electrodynamic spraying techniques or other low volume methods.

The term "plant" as used herein includes seedlings, bushes and trees. Furthermore, the fungicidal method of the invention includes preventative, protectant, prophylactic and eradicant treatments.

The compounds are preferably used for agricultural and horticultural purposes in the form of a composition. The type of composition used in any instance will depend upon the particular purpose envisaged.

The compositions may be in the form of dustable powders or granules comprising the active ingredient (invention compound) and a solid diluent or carrier, for example, fillers such as kaolin, bentonite, kieselguhr, dolomite, calcium carbonate, talc, powdered magnesia, fuller's earth, gypsum, diatomaceous earth and china clay. Such granules can be preformed granules suitable for application to the soil without further treatment. These granules can be made either by impregnating pellets of filler with the active ingredient or by pelleting a mixture of the active ingredient and powdered filler. Compositions for dressing seed may include an agent (for example, a mineral oil) for assisting the adhesion of the composition to the seed; alternatively the active ingredient can be formulated for seed dressing purposes using an organic solvent (for example, N-methylpyrrolidone, propylene glycol or dimethylformamide). The compositions may also be in the form of wettable powders or water dispersible granules comprising wetting or dispersing agents to facilitate the dispersion in liquids. The powders and granules may also contain fillers and suspending agents.

Emulsifiable concentrates or emulsions may be prepared by dissolving the active ingredient in an organic solvent optionally containing a wetting or emulsifying agent and then adding the mixture to water which may also contain a wetting or emulsifying agent. Suitable organic solvents are aromatic solvents such as alkylbenzenes and alkylnaphthalenes, ketones such as cyclohexanone and methylcyclohexanone, chlorinated hydrocarbons such as chlorobenzene and trichlorethane, and alcohols such as benzyl alcohol, furfuryl alcohol, butanol and glycol ethers.

Suspension concentrates of largely insoluble solids may be prepared by ball or bead milling with a dispersing agent with a suspending agent included to stop the solid settling.

Compositions to be used as sprays may be in the form of aerosols wherein the formulation is held in a container under pressure of a propellant, e.g. fluorotrichloromethane or dichlorodifluoromethane.

The invention compounds can be mixed in the dry state with a pyrotechnic mixture to form a composition suitable for generating in enclosed spaces a smoke containing the compounds.

Alternatively, the compounds may be used in microencapsulated form. They may also be formulated in biodegradable polymeric formulations to obtain a slow, controlled release of the active substance.

By including suitable additives, for example additives for improving the distribution, adhesive power and resistance to rain on treated surfaces, the different compositions can be better adapted for various utilities.

The invention compounds can be used as mixtures with fertilisers (e.g. nitrogen-, potassium- or phosphorus-containing fertilisers). Compositions comprising only granules of fertiliser incorporating, for example coated with, the compound are preferred. Such granules suitably contain up to 25% by weight of the compound. The invention therefore also provides a fertiliser composition comprising a fertiliser and the compound of general formula (I) or a salt or metal complex thereof.

Wettable powders, emulsifiable concentrates and suspension concentrates will normally contain surfactants, e.g. a wetting agent, dispersing agent, emulsifying agent or suspending agent. These agents can be cationic, anionic or non-ionic agents.

Suitable cationic agents are quaternary ammonium compounds, for example, cetyltrimethylammonium bromide. Suitable anionic agents are soaps, salts of aliphatic monoesters of sulphuric acid (for example, sodium lauryl sulphate), and salts of sulphonated aromatic compounds (for example, sodium dodecylbenzenesulphonate, sodium, calcium or ammonium lignosulphonate, butylnaphthalene sulphonate, and a mixture of sodium diisopropyl- and triisopropyl- naphthalene sulphonates).

Suitable non-ionic agents are the condensation products of ethylene oxide with fatty alcohols such as oleyl or cetyl alcohol, or with alkyl phenols such as octyl- or nonylphenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example, polyvinylpyrrolidone and sodium carboxymethylcellulose), and swelling clays such as bentonite or attapulgite.

Compositions for use as aqueous dispersions or emulsions are generally supplied in the form of a concentrate containing a high proportion of the active ingredient, the concentrate being diluted with water before use. These concentrates should preferably be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 10-85%, for example 25-60%, by weight of the active ingredient. After dilution to form aqueous preparations, such preparations may contain varying amounts of the active ingredient depending upon the intended purpose, but an aqueous preparation containing 0.0005% or 0.01% to 10% by weight of active ingredient may be used.

The compositions of this invention may contain other compounds having biological activity, e.g. compounds having similar or complementary fungicidal activity or which possess plant growth regulating, herbicidal or insecticidal activity.

A fungicidal compound which may be present in the composition of the invention may be one which is capable of combating ear diseases of cereals (e.g. wheat) such as *Septoria, Gibberella* and *Helminthosporium* spp., seed and soil-borne diseases and downy and powdery mildews on grapes and powdery mildew and scab on apple, etc. By including another fungicide, the composition can have a broader spectrum of activity than the compound of general formula (I) alone. Further the other fungicide can have a synergistic effect on the fungicidal activity of the compound of general formula (I). Examples of fungicidal compounds which may be included in the composition of the invention are (RS)-1-aminopropylphosphonic acid, (RS)-4-(4-chlorophenyl)-2-phenyl-2-(1H-1,2,4-triazol-1-yl-methyl)butyronitrile, (Z)-N-but-2-enyloxymethyl 2-chloro-2',6'-diethylacetanilide, 1-(2-cyano-2-methoxyimino-acetyl)-3-ethyl urea, 1-[(2RS,4RS;2RS,4RS)-4-bromo-2-(2,4-dichlorophenyl)tetrahydrofurfuryl]-1H-1,2,4-triazole, 3-(2,4-dichlorophenyl)-2-(1H-1,2,4-triazol-1-yl)quinazolin-4(3H)-one, 3-chloro-4-[4-methyl-2-(1H-1,2,4-triazol-1-methyl)-1,3-dioxolan-2-yl]phenyl-4-chlorophenyl ether, 4-bromo-2-cyano-N,N-dimethyl-6-trifluoromethylbenzimidazole-1-sulphonamide, 5-ethyl-5,8 dihydro-8-oxo(1,3)dioxolo(4,5-g)quinoline-7-carboxylic acid, α-[N-(3-chloro-2,6-xylyl)-2-methoxyacetamido]-γ-butyrolactone, aldimorph, anilazine, benalaxyl, benomyl, biloxazol, binapacryl, bitertanol, blasticidin S, bupirimate, buthiobate, captafol, captan, carbendazim, carboxin, chlorbenz-thiazone, chloroneb, chlorothalonil, chlorozolinate, copper containing compounds such as copper oxychloride, copper sulphate and Bordeaux mixture, cycloheximide, cymoxanil, cyproconazole, cyprofuram, di-2-pyridyl disulphide 1,1'-dioxide, dichlofluanid, dichlone, diclobutrazol, diclomezine, dicloran, difenoconazole, dimethamorph, dimethirimol, diniconazole, dinocap, ditalimfos, dithianon, dodemorph, dodine, edifenphos, etaconazole, ethirimol, ethyl (Z)-N-benzyl-N-([methyl(methylthioethylideneamino-oxycarbonyl)amino]thio)-β-alaninate, etridiazole, fenapanil, fenarimol, fenfuram, fenpiclonil, fenpropidin, fenpropimorph, fentin acetate, fentin hydroxide, flutolanil, flutriafol, flusilazole, folpet, fosetyl-aluminium, fuberidazole, furalaxyl, furconazole-cis, guazatine, hexaconazole, hydroxyisoxazole, imazalil, imibenconazole, iprobenfos, iprodione, isoprothiolane, kasugamycin, mancozeb, maneb, mepanipyrim, mppronil, metalaxyl, methfuroxam, metsulfovax, myclobutanil, N-(4-methyl-6-prop-1-ynylpyrimidin-2-yl)aniline, neoasozin, nickel dimethyldithiocarbamate, nitrothal-isopropyl, nuarimol, ofurace, organomercury compounds, oxadixyl, oxycarboxin, pefurazoate, penconazole, pencycuron, phenazin oxide, phthalide, polyoxin D, polyram, probenazole, prochloraz, procymidone, propamocarb, propiconazole, propineb, prothiocarb, pyrazophos, pyrifenox, pyroquilon, pyroxyfur, pyrrolnitrin, quinomethionate, quintozene, SSF-109, streptomycin, sulphur, tebuconazole, techlofthalam, tecnazene, tetra-conazole, thiabendazole, thicyofen, thiophanate-methyl, thiram, tolclofos-methyl, triacetate salt of 1,1'-iminodi(octa-methylene)diguanidine, triadimefon, triadimenol, triazbutyl, tricyclazole, tridemorph, triforine, validamycin A, vinclozolin, zarilamid nd zineb. The compounds of general formula (I) can be mixed with soil, peat or other rooting media for the protection of plants against seed-borne, soil-borne or foliar fungal diseases.

Suitable insecticides which may be incorporated in the composition of the invention include buprofezin, carbaryl, carbofuran, carbosulfan, chlorpyrifos, cycloprothrin, demeton-s-methyl, diazinon, dimethoate, ethofenprox, fenitrothion, fenobucarb, fenthion, formothion, isoprocarb, isoxathion, monocrotophos, phenthoate, pirimicarb, propaphos and XMC.

Plant growth regulating compounds are compounds which control weeds or seedhead, formation, or selectively control the growth of less desirable plants (e.g. grasses).

Examples of suitable plant growth regulating compounds for use with the invention compounds are 3,6-dichloropicolinic acid, 1-(4-chlorophenyl)-4,6-dimethyl-2-oxo-1,2-dihydropyridine-3-carboxylic acid, methyl-3,6-dichloroanisate, abscisic acid, asulam, benzoylprop-ethyl, carbetamide, daminozide, difenzoquat, dikegulac, ethephon, fenpentezol, fluoridamid, glyphosate, glyphosine, hydroxybenzonitriles (e.g. bromoxynil), inabenfide, isopyrimol, long chain fatty alcohols and acids, maleic hydrazide, mefluidide, morphactins (e.g. chlorfluoroecol), paclobutrazol, phenoxyacetic acids (e.g. 2,4-D or MCPA), substituted benzoic acid (e.g. triiodobenzoic acid), substituted quaternary ammonium and phosphonium compounds (e.g. chloromequat, chlorphonium or mepiquatchloride), tecnazene, the auxins (e.g. indoleacetic acid, indolebutyric acid, naphthylacetic acid or naphthoxyacetic acid), the cytokinins (e.g. benzimidazole, benzyladenine, benzylaminopurine, diphenylurea or kinetin), the gibberellins (e.g. $GA_3$, $GA_4$ or $GA_7$) and triapenthenol.

The following Examples illustrate the invention.

EXAMPLE 1

This Example illustrates the preparation of N-(2-methoxy-5-pyridyl)-1-fluorocyclopropanecarboxamide (Comound No 1 in Table I).

1-Fluorocyclopropylmethylketone was prepared as in Synthesis p. 189 (1977). The crude ketone (1.2 g, 11.8 mmoles) was added dropwise to an aqueous solution of sodium hypobromite (prepared from 12.4 g sodium hydroxide and 4 ml bromine) at 0° C. The mixture was stirred at 25° C. for 4½]hours poured onto ice and acidified to a methyl orange endpoint with 5% aqueous hydrochloric acid. The acid was extracted with 40 ml ether; the extract was dried over anhydrous magnesium sulphate, filtered and concentrated in vacuo to give crude 1-fluorocyclopropane carboxylic acid. Yield 0.84 g, 70% pure by gc analysis.

1-Fluorocyclopropanecarboxylic acid (crude) (0.84 g, 0.0081 moles) was added in two portions to a solution of methylene chloride (50 ml ) and carbonyl diimidazole (1.31 g, 0.0081 moles). The reaction was allowed to stand for 1 hour and then 5-amino-2-methoxypyridine (0.83 ml , 0.0081 moles) was added to it in one portion. The reaction mixture was allowed to stand at room temperature for 1 hour. The reaction mixture was then washed with saturated sodium bicarbonate (50 ml ), 5% hydrochloric acid (20 ml ) and saturated sodium bicarbonate solution (25 ml ); dried over anhydrous magnesium sulfate, filtered and evaporated in vacuo to give 0.5 g of crude N-(2-methoxy-5-pyridyl)-1-fluorocyclopropanecarboxamide.

The prior acid wash was extracted with methylene chloride (3 × 50 ml ); and the extract washed with saturated sodium bicarbonate, dried over anhydrous magnesium sulfate and evaporated in vacuo to give 0.2 g of pure product.

EXAMPLE 2

This Example illustrates the preparation of 1-fluorocyclopropane carboxylic acid.

A solution of sodium hypobromite was prepared in situ by adding bromine (19.66 g) dropwise, to a solution of sodium hydroxide (19.67 g) in water (100 ml ), at 0°–10° C. On complete addition the solution was cooled to 0° C.

Pure 1-fluorocyclopropyl methyl ketone (1.90 g) was added dropwise over one minute. On complete additon the reaction mixture was allowed to warm to room temperature and stirred for 3½ hours.

The reaction mixture was poured onto ice chips and acidified to pH 3.5 with 5% aqueous hydrochloric acid solution. Excess bromine was removed by adding sodium bisulphite until the brown colour disappeared. The mixture was extracted with diethyl ether (three times). The organic phases were combined and washed with saturated brine solution. The organic extracts were dried (anhydrous magnesium sulphate), filtered, and the solvent removed by rotary evaportion under reduced pressure at 40° to afford the title compound as a clear colourless oil (1.25 g).

$^1$H NMR (CDCl$_3$): δ1.44(s,2H); 1.50(d,2H); 9.53(br.s,1H) ppm.

EXAMPLE 3

This Example illustrates the preparation of 2,2-difluorocyclopropane carboxylic acid.

A mixture of potassium permanganate (3.49 g), water (25 ml) and 2,2-difluoro-1-vinyl cyclopropane (1.15 g) was stirred at room temperature for 18 hours. The mixture was filtered. The filtrate was acidified with 20% hydrochloric acid (100 ml) and extracted with dichloromethane (4×100 ml). The combined organic extracts were washed with saturated brine solution (50 ml) and dried over anhydrous magnesium sulphate. Filtration, followed by removal of solvent from the filtrate by rotary evaporation under reduced pressure at 46° C. afforded the title compound as a clear colourless oil (1.17 g). Literature references: EP 0 351 647 A2 and Chem. Ber. 109, (1976), 2350.]

$^1$H NMR (CDCl$_3$): δ1.75–1.90(c,1H); 2.04–2.16(c,1H); 2.18(s,1H); 2.40-2.51(c.1H) ppm.

EXAMPLE 4

This Example illustrates the preparation of 2,2-difluoro-1-methylcyclopropane carboxylic acid.

A mixture of 2,2-difluoro-1-methyl-1-vinyl cyclopropane (2 g), potassium permanganate (5.36 g) and water (24 ml) was stirred at room temperature for 24 hours.

The mixture was filtered. The filtrate was acidified to pH2 with concentrated hydrochloric acid and extracted with diethyl ether. The combined organic extracts were dried over anhydrous magnesium sulphate. Filtration, followed by removal of solvent from the filtrate by rotary evaporation under reduced pressure at 40° C. the title compound as afforded a white solid (1.25 g).

$^1$H NMR (CDCl$_3$): δ1.35–1.42(c,1H); 1.45(c,3H); 2.20-2.31(c,1H) ppm. (Acidic proton not observed.)

EXAMPLE 5

This Example illustrates the preparation of 2-chloro-2-fluorocyclopropane carboxylic acid.

A mixture of potassium permanganate (21.69 g), water (200 ml) and 1-chloro-1-fluoro-2-vinylcyclopropane (8.27 g) was stirred at room temperature for 24 hours. The mixture was filtered. The filtrate was acidified to pH2 with concentrated hydrochloric acid and extracted with dichloromethane (three times). The combined organic extracts were washed with saturated brine solution and dried over anhydrous magnesium sulphate. Filtration, followed by removal of solvent from the filtrate by rotary evaporation under reduced pressure at 40° C. afforded the title compound as a clear colourless oil (4.49 g). Literature reference: Chem Ber (1976), 109, 2350.]

$^1$H NMR (CDCl$_3$): δ1.62–2.05(c,1H); 2.21–2.64(c,1H); 2.70(c,1H) ppm. (Acidic proton not observed.)

EXAMPLE 6

This Example illustrates the preparation of 2-chloro-2-fluoro-1-methyl cyclopropate carboxylic acid.

A mixture of potassium permanganate (28.45 g), water (200 ml) and 2-chloro-2-fluoro-1-methyl-1-vinyl cyclopropane (12.11 g) was stirred at room temperature for 24 hours. The mixture was filtered. The filtrate was acidified to pH2 with concentrated hydrochloric acid and extracted with diethyl ether (three times). The combined organic extracts were washed with saturated brine solution and dried over anhydrous magnesium sulphate. Filtration, followed by removal of solvent from the filtrate by rotary evaporation under reduced pressure at 40° C. afforded the title compounds a clear colourless oil (9.33 g). [Literature reference is EP 0351647 A2.]

$^1$H NMR (CDCl$_3$): δ1.29–1.60(c,4H); 2.07–2.50(c,1H) ppm. (Acidic proton not observed.)

EXAMPLE 7

This Example illustrates the preparation of 2,2-dichloro-1-methylcyclopropane carbonyl chloride.

Oxalyl chloride (20.23 g) was added to 2,2-dichloro-1-methylcyclopropane carboxylic acid (8.45 g) at room temperature. The mixture was stirred for 18 hours. Excess oxalyl chloride was removed by distillation at atmosphere pressure (63°–65° C.). The product was distilled at atmosphere pressure (184° C.) to afford the title compound as a clear oil (7.18 g) which turned brown on standing.

$^1$H NMR (CDCl$_3$): δ1.63(d,1H); 1.77(s,3H); 2.38(d,1H) ppm.

EXAMPLE 8

This Example illustrates the preparation of N-(2-methoxy-5-pyridyl)-1-fluorocyclopropane carboxamide (Compound No 1 in Table I).

To a solution of 5-amino-2-methoxypyridine (1.19 g) and 4-dimethylaminopyridine (0.195 g) in dry dichloromethane (40 ml) at room temperature, was added 1-fluorocyclopropane carboxylic acid (1.0 g) and 1-ethyl-3-(3-dimethylaminopropyl)carbodiimide hydrochloride (1.84 g). The resultant reaction mixture was stirred at room temperature for 17 hours. The reaction mixture was poured into water and extracted with dichloromethane (three times). The extracts were combined and dried over anhydrous magnesium sulphate. Filtration, followed by removal of solvent from the filtrate by rotary evaporation afforded a brown oil which was purified by flash chromatography from silica using n-hexane:diethyl ether (1:1) as eluent. Recrystallisation was achieved from petroleum ether (60°–80° C.) to afford the title compound as a white solid (356mg).

EXAMPLE 9

This Example illustrates the preparation of N-(2-fluoro-5-pyridyl)-1-fluorocyclopropane carboxamide (Compound No 3 in Table I).

To a solution of 5-amino-2-fluoropyridine (1.34 g) and 4-dimethylaminopyridine (0.248 g) in dry dichloromethane (40 ml) at room temperature, was added 1- fluorocyclopropane carboxylic acid (1.25 g) and 1-ethyl-3-(3-dimethylaminopropyl)carbodiimide hydrochloride (2.31 g). The resultant reaction mixture was stirred at room temperature for 24 hours. The reaction mixture was poured into water and extracted with dichloromethane (three times). The extracts were combined and dried over anhydrous magnesium sulphate. Filtration, followed by removal of solvent from the filtrate by rotary evaporation afforded a brown oil which was purified by flash chromatography from silica using n-hexane:ethyl acetate (2:1) as eluent. Recyrstallisation was achieved from n-hexane/ethyl acetate to afford the title compound as a white solid (65mg).

EXAMPLE 10

This Example illustrates the preparation of N-(2-methoxy-5-pyridyl)-1-bromocyclopropane carboxamide (Compound No 10 in Table I).

To a mixture of a 5-amino-2-methoxypyridine (0.767 g), triethylamine (10 ml ) and dry dichloromethane (40 ml ) was added 1-bromocyclopropanecarbonyl chloride (1 g). An exotherm was observed (about +10° C.). The reaction mixture was stirred for 24 hours.

The reaction mixture was poured into water and extracted with dichloromethane (three times). The combined organic extracts were washed with 5% hydrochloric acid, dried (anhydrous magnesium sulphate) and decolourized (activated charcoal). The mixture was filtered and the solvent removed from the filtrate by rotary evaporation under reduced pressure at 40° C., to afford an oil. The oil was purified by flash chromatography through a silica column eluted with n-hexane:ethyl acetate (3:1) followed by recrystallisation from n-hexane/diethyl ether to afford the title compound as a white solid (0.846 g).

EXAMPLE 11

This Example illustrates the preparation of N-(2-methoxy-5-pyridyl)-2,2-difluorocyclopropane carboxamide (Compound No 5 in Table I).

to a solution of 5-amino-2-methoxypyridine (0.305 g) and 4-dimethylaminopyridine (0.03 g) in dry dichloromethane (10 ml ) at room temperature, was added 2,2-difluorocyclopropane carboxylic acid (0.3 g) and 1-ethyl-3-(3-dimethylaminopropyl)carbodiimide hydrochloride (0.472 g). The resultant reaction mixture was stirred at room temperature for 24 hours. The reaction mixture was poured into water and extracted with dichloromethane (three times). The combined organic extracts dried over anhydrous magnesium sulphate. Filtration, followed by removal of solvent from the filtrate by rotary evaporation afforded a brown oil which was purified by flash chromatography from silica using n-hexane/ethyl acetate (1:1) as eluent. Recyrstallisation was achieved from n-hexane/ethyl acetate to afford the title compound a white solid (123 mg).

EXAMPLE 12

This Example illustrates the preparation of N-(2-methoxy-5-pyridyl)-2-fluorocyclopropane carboxamide (Compound Nos 17 and 18 in Table I).

N-(2-methoxy-5-pyriyyl)-2-chloro-2-fluorocyclopropane carboxamide (0.3 g), ethanol (10 ml ), ethylene diamine (0.2 g) and Raney Nickel (0.5 g) were placed in an autoclave. The mixture was heated to 120° C. with an atmosphere of 34 bars of hydrogen for 16 hours.

The reaction mixture was poured into ethyl acetate and filtered. Removal of solvents from the filtrate by rotary evaporation under reduced pressure at 40° C. afforded a brown oil which was found to comprise 4 diastereomers: (1R,2S), (1S, 2R), (1R,2R) and (1S,2S). Two pairs of enantiomers were separated by flash chromatography through a silica column eluted with n-hexane/ethyl acetate (1:1). The two isolated racemates were:

Racemate A (Compoound No 17 of Table I) comprising N-(2-methoxy-5-pyridyl)-(1R,2R)-2-fluorocyclopropane carboxamide, and N-(2-methoxy-5-pyridyl)-(1S,1R)-2-fluoroclopropane carboxamide; and Racemate B (Compound No 18 in Table I) comprising N-(2-methoxy-5-pyridyl)-(1S,2R)-2-fluoroclopropane carboxamide, and N-(2-methoxy-5-pyridyl)-(1R,2S)-2-fluorocyclopropane carboxamide.

Both racemates were recrystallised from n-hexane/ethyl acetate.

[This method of hydrodechlorination was adapted from a patent EP 0351650 A2].

EXAMPLE 13

This Example illustrates the preparation N-(2-methoxy-5-pyridyl)-2,2-difluoro-1-methylcyclopropane carboxamide (Compound No 23 in Table I).

To a solution of 5-amino-2-methoxypyridine (0.364 g) and 4-dimethylaminopyridine (0.037 g) in dry dichloromethane (10 ml ) at room temperature, was added 2,2-difluoro-1-methylcyclopropane carboxylic acid (0.400 g) and 1-ethyl-3-(3-dimethylaminopropyl)carbodiimide hydrochloride (0.565 g). The resultant reaction mixture was stirred at room temperature for 24 hours. The reaction mixture was poured into water and extracted with dichloromethane (three times). The organic extracts were combined and was dried over anhydrous magnesium sulphate. Filtration, followed by removal of solvent from the filtrate by rotary evaporation afforded a brown oil which was purified by flash chromatography from silica using n-hexane:ethyl acetate (1:1) as eluent. Recrystallisation was achieved from n-hexane/ethyl acetate to afford the title compound as a while solid (360 mg).

EXAMPLE 14

This Example illustrates the preparation of N-(2-methoxy-5-pyridyl)-2-chloro-2-fluorocyclopropane carboxamide (Compound No 26 in Table I).

To a solution of 5-amino-2-methoxypyridine (0.537 g) and 4-dimethylaminopyridine (0.053 g) in dry dichloromethane (10 ml ) at room temperature, was added 2-chloro-2-fluoro-cyclopropane carboxylic acid (0.6 g) and 1-ethyl-3-(3-dimethylaminopropyl)carbodiimide hydrochloride (1.25 g). The resultant reaction mixture was stirred at room temperature for 72 hours. The reaction mixture was poured into water and extracted with dichloromethane (three times). The organic extracts were combined and was dried over anhydrous magnesium sulphate. Filtration, followed by removal of solvent from the filtrate by rotary evaporation afforded a brown oil which was purified by flash chromatography from silica using n-hexane:ethyl acetate (1:1) as eluent. Recrystallization was achieved from n-hexane/ethyl acetate to afford the title compound as a white solid (392 mg).

EXAMPLE 15

This Example illustrates the preparation of N-(2-methoxy-5-pyridyl)-2-chloro-2-fluoro-1-methylpropane carboxamide (Compound No 29 in Table I).

To a solution of 5-amino-2-methoxypyridine (0.33 g) and 4-dimethylaminopyridine (0.025 g) in dry dichloromethane (10 ml) at room temperature, was added 2-chloro-2-fluoro-1-methylcyclopropane carboxylic acid (0.4 g) and 1-ethyl-3-(3-dimethylaminopropyl)carbodiimide hydrochloride (1.01 g). The resultant reaction mixture was stirred at room temperature for 24 hours. The reaction mixture was poured into water and extracted with dichloromethane (three times). The organic extracts were combined and dried over anhydrous magnesium sulphate. Filtration, followed by removal of solvent from the filtrate by rotary evaporation afforded a brown oil which was purified by flash chromatography from silica using n-hexane:ethyl acetate (1:1) as eluent afforded the title compound as a brown oil (470 mg).

EXAMPLE 16

This Example illustrates the preparation of N-(2-methoxy-5-pyridyl)-2,2-dichloro-1-methylcyclopropane carboxamide (Compound No 32 in Table I).

To a solution of 5-amino-2-methoxypyridine (4.96 g) and 4-dimethylaminopyridine (0.488 g) in dry dichloromethane (100 ml) at room temperature, was added 2,2-dichloro-1-methylcyclopropane carboxylic acid (4.88 g, ex Aldrich) and 1-ethyl-3-(3-dimethylaminopropyl)carbdiimide hydrochloride (7.68 g). The resultant reaction mixture was stirred at room temperature for 18 hours. The reaction mixture was poured into water and extracted with dichloromethane (three times). The organic extracts were combined and dried over anhydrous magnesium sulphate. Filtration, followed by removal of solvent from the filtrate by rotary evaporation afforded a brown oil which was purified by recrystallisation from n-hexane/ethyl acetate to afford the title compound as a white solid (3.48 g).

EXAMPLE 17

This Example illustrtes the preparation of N-methyl-N-(2-methoxy-5-pyridyl)-1-fluorocyclopropane carboxamide (Compound No 35 in Table I).

To a mixture of potassium hydroxide (0.203 g) and dimethylsulphoxide (10 ml) was added a solution of N-(2-methoxy-5-pyridyl)-1-fluorocyclopropane carboxamide (0.19 g) in dimethylsulphoxide (5 ml). A solution of methyl iodide (0.257 g) in dimethylsulphoxide (5 ml) was added to the reaction mixture. The reaction mixture was stirred at room temperature for 16 hours.

The reaction mixture was poured into water and extracted with dichloromethane (three times). The combined organic extracts were washed with water and dried over anhydrous magnesium sulphate. Filtration, followed by removal of solvent from the filtrate by rotary evaporation under reduced pressure at 40° C. afforded an oil which was purified by flash chromatography through a silica column eluted with n-hexane:diethyl ether (3:1) to afford the title compound as a light yellow oil (95 mg).

EXAMPLE 18

This Example illustrates the preparation of N-propargyl-N-(2-methoxy-5-pyridyl)-1-fluorocyclopropane carboxamide (Compound No 38 in Table I).

To a mixture of potassium hydroxide (0.18 g) and dimethylsulphoxide (10 ml) was added a solution of N-(2-methoxy-5-pyridyl)-1-fluorocyclopropane carboxamide (0.17 g) in dimethylsulphoxide (5 ml). A solution of propargyl bromide (0.24 g) in dimethylsulphoxide (5 ml) and toluene (5 ml) was added to the reaction mixture. The reaction mixture was stirred at room temperature for 24 hours.

The reaction mixture was poured into water and extracted with dichloromethane (three times). The combined organic extracts were washed with water and dried over anhydrous magnesium sulphate. Filtration, followed by removal of solvent from the filtrate by rotary evaporation under reduced pressure at 40° C. afforded an oil which was purified by flash chromatography through a silica column eluted with n-hexane:diethyl ether (3:1) to afford the title compound as a yellow oil (0.128 g).

EXAMPLE 19

This Example illustrates the preparation of N-allyl-N-(2-methoxy-5-pyridyl)-1-fluorocyclopropane carboxamide (Compound No 41 in Table I).

To a mixture of potassium hydroxide (0.16 g) and dimethylsulphoxide (10 ml) was added a solution of N-(2-methoxy-5-pyridyl)-1-fluorocyclopropane carboxamide (0.15 g) in dimethylsulphoxide (5 ml). A solution of allyl bromide (0.173 g) in dimethylsulphoxide (5 ml) was added to the reaction mixture. The reaction mixture was stirred at room temperature for 24 hours.

The reaction mixture was poured into water and extracted with dichloromethane (three times). The combined organic extracts were washed with water and dried over anhydrous magnesium sulphate. Filtration, followed by removal of solvent from the filtrate by rotary evaporation under reduced pressure to 40° C. afforded an oil which was purified by flash chromatography through a silica column eluted with n-hexane:ethyl acetate (3:1) to afford the title compound as an orange oil (0.132 g).

EXAMPLE 20

This Example illustrates the preparation of N-benzyl-N-(2-methoxy-5-pyridyl)-1-fluorocyclopropane carboxamide (Compound No 44 in Table I).

To a mixture of potassium hydroxide (0.173 g) and dimethylsulphoxide (10 ml) was added a solution of N-(2-methoxy-5-pyridyl)-1-fluorocyclopropane carboxamide (0.163 g) in dimethylsulphoxide (5 ml). A solution of benzyl bromide (0.265 g) in dimethylsulphoxide (5 ml) was added to the reaction mixture. The reaction mixture was stirred at room temperature for 4 hours.

The reaction mixture was poured into water and extracted with dichloromethane (three times). The combined organic extracts were washed with water and dried over anhydrous magnesium sulphate. Filtration, followed by removal of solvent from the filtrate by rotary evaporation under reduced pressure at 40° C. afforded an oil which was purified by flash chromatography through a silica column eluted with n-hexane:diethyl ether (6:4) to afford a pale yellow oil (140 mg).

EXAMPLE 21

This Example illustrates the preparation of N-but-2-ynyl-N-(2-methoxy-5-pyridyl)-1-fluorocyclopropane carboxamide (Compound No 47 in Table I).

To a mixture of potassium hydroxide (0.436 g) and dimethylsulphoxide (10 ml) was added a solution of N-(2-methoxy-5-pyridyl)-1-fluorocyclopropane carboxamide (0.41 g) in dimethylsulphoxide (5 ml). A solution of methyl propargyl bromide (0.52 g) in dimethylsulphoxide (5 ml) was added to the reaction mixture. The reaction mixture was stirred at room temperature for 3 hours.

The reaction mixture was poured into water and extracted with dichloromethane (three times). The combined organic extracts were washed with water and dried over anhydrous magnesium sulphate. Filtration, followed by removal of solvent from the filtrate by rotary evaporation under reduced pressure at 40° C. afforded an oil which was purified by flash chromatography through a silica column eluted with n-hexane:-diethyl ether (6:4) to afford a colourless crystalline solid. Recrystallisation from n-hexane afforded the title compound as a white solid (301 mg).

The following are examples of compositions suitable for agricultural and horticultural purposes which can be formulated from the compounds of the invention. Such compositions form another aspect of the invention. Percentages are by weight.

EXAMPLE 22

An emulsifiable concentrate is made up by mixing and stirring the ingredients until all are dissolved.

| Compound No. 1 of Table I | 10% |
| --- | --- |
| Benzyl alcohol | 30% |
| Calcium dodecylbenzenesulphonate | 5% |
| Nonylphenolethoxylate (13 moles ethylene oxide) | 10% |
| Alkyl benzenes | 45% |

EXAMPLE 23

The active ingredient is dissolved in methylene dichloride and the resultant liquid sprayed on to the granules of attapulgite clay. The solvent is then allowed to evaporate to produce a granular composition.

| Compound No. 1 of Table I | 5% |
| --- | --- |
| Attapulgite granules | 95% |

EXAMPLE 24

A composition suitable for use as a seed dressing is prepared by grinding and mixing the three ingredients.

| Compound No. 1 of Table I | 50% |
| --- | --- |
| Mineral oil | 2% |
| China clay | 48% |

EXAMPLE 25

A dustable powder is prepared by grinding and mixing the active ingredient with talc.

| Compound No. 1 of Table I | 5% |
| --- | --- |
| Talc | 95% |

EXAMPLE 26

A suspension concentration is prepared by ball milling the ingredients to form an aqueous suspension of the ground mixture with water.

| Compound No. 1 of Table I | 40% |
| --- | --- |
| Sodium lignosulphonate | 10% |
| Bentonite clay | 1% |
| Water | 49% |

This formation can be used as a spray by diluting into water or applied directly to seed.

EXAMPLE 27

A wettable powder formulation is made by mixing together and grinding the ingredients until all are thoroughly mixed.

| Compound No. 1 of Table I | 25% |
| --- | --- |
| Sodium lauryl sulphate | 2% |
| Sodium lignosulphonate | 5% |
| Silica | 25% |
| China clay | 43% |

EXAMPLE 28

The compounds were tested against a variety of foliar fungal diseases of plants. The technique employed was as follows.

The plants were grown in John Innes Potting Compost (No 1 or 2) in 4 cm diameter minipots. The test compounds were formulated either by bead milling with aqueous Dispersol T or as a solution in acetone or acetone/ethanol which was diluted to the required concentration immediately before use. For the foliage diseases, the formulations (100 ppm active ingredient) were sprayed onto the foliage and applied to the roots of the plants in the soil. The sprays were applied to maximum retention and the root drenches to a final concentration equivalent to approximately 40 ppm a.i. in dry soil. Tween 20, to give a final concentration of 0.05%, was added when the sprays were applied to cereals.

For most of the tests the compound was applied to the soil (roots) and to the foliage (by spraying) one or two days before the plant was inoculated with the disease. An exception was the test on *Erysiphe graminis* in which the plants were inoculated 24 hours before treatment. Foliar pathogens were applied by spray as spore suspensions onto the leaves of test plants. After inoculation, the plants were put into an appropriate environment to allow infection to proceed and then incubated until the disease was ready for assessment. The period between inoculation and assessment varied from four to fourteen days according to the disease and environment.

The disease control was recorded by the following grading:
4 = no disease
3 = trace −5% of disease on untreated plants
2 = 6–25% of disease on untreated plants
1 = 26–59% of disease on untreated plants
0 = 60–100% of disease on untreated plants
The results are shown in Table III.

TABLE III

| Compound No | Puccinia recondita (Wheat) | Erysiphe graminis hordei (Barley) | Venturia inaequalis (Apple) | Pyricularia oryzae (Rice) | Cercospora arachidicola (Peanut) | Plasmopara viticola (Vine) | Phytophthora infestans (Tomato) | Erysiphe graminis tritici (Wheat) |
|---|---|---|---|---|---|---|---|---|
| 1  | 4 | 4 | 4 | 2 | 0 | 0 | 0 |   |
| 3  |   | 4 | 4 | 4 |   | 0 | 0 |   |
| 5  | 4 |   | 4 | 3 |   | 0 | 0 | 4 |
| 10 | 1 | 3 | 0 | 0 |   | 0 | 0 |   |
| 23 | 0 |   |   | 0 |   | 1 |   | 0 |
| 24 | 0 |   |   | 0 |   | 1 |   | 0 |
| 29 | 0 |   | 0 | 0 |   | 0 | 0 | 4 |
| 32 | 0 | 0 | 1 | 0 |   | 0 | 0 |   |
| 34 | 0 | 2 | 4 | 0 | 0 | 0 | 0 |   |
| 35 |   |   |   |   |   |   |   | 4* |
| 38 | 4 |   | 4 | 0 |   | 2 | 0 | 4 |
| 44 | 4 |   | 0 |   |   | 0 | 0 | 4 |
| 47 | 4 |   | 0 |   |   | 0 | 0 | 4 |

*tested at 25 ppm only

We claim:

1. Compounds of formula (I):

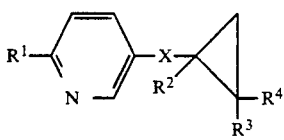

or a stereoisomer thereof, wherein $R^1$ is hydrogen, halogen, $C_{1-4}$ alkoxy, $C_{1-4}$ alkyl, $C_{2-4}$ alkenyl, $C_{2-4}$ alkynyl, $C_{1-4}$ haloalkyl, $C_{1-4}$ haloalkoxy, —COR or cyano; $R^2$, $R^3$ and $R^4$ are independently hydrogen, halogen or methyl, provided that $R^2$, $R^3$ and $R^4$ are not all hydrogen and provided that when one of them is methyl then at least one of the other two is not hydrogen and further provided that when any two of $R^2$, $R^3$ or $R^4$ are methyl then the other is not hydrogen X is

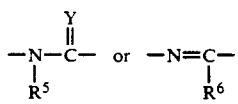

wherein $R^5$ is hydrogen, $C_{1-4}$ alkyl (optionally substituted by hydrogen or cyano), benzyl (wherein the phenyl moiety is optionally substituted by halogen, alkyl, haloalkyl, alkoxy, haloalkoxy, cyano or nitro), $C_{2-4}$ alkenyl, $C_{2-4}$ alkynyl, cyano, —COR, $C_{1-4}$ thioalkoxy, $C_{1-4}$ thiohaloalkoxy or —SNR$^7$R$^8$; $R^7$ and $R^8$ are independently $C_{1-4}$ alkyl or —CO$_2$R; Y is oxygen or sulphur; $R^6$ is $C_{1-4}$ alkoxy, $C_{1-4}$ thioalkoxy or —NR$^9$R$^{10}$; and $R^9$ and $R^{10}$ are independently hydrogen, $C_{1-4}$ alkyl, aryl or arlalkyl or $R^9$ and $R^{10}$ join to form an aziridine, azetidine, pyrrolidine, piperidine, hexamethyleneimine, morpholine, imidazole, pyrazole, 1,2,4-triazole, 1,2,3-triazole, pyrrole or tetrazole ring; and R is $C_{1-4}$ alkyl or $C_{3-7}$ cycloalkyl.

2. A compound as claimed in claim 1 having the formula (I):

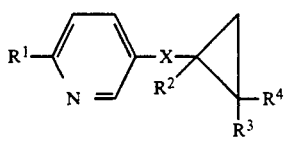

or a stereoisomer thereof, wherein $R^1$ is hydrogen, fluorine, chlorine or $C_{1-4}$ alkoxy; $R^3$ and $R^4$ are independently hydrogen, methyl, chlorine, fluorine or bromine; $R^2$ is hydrogen or methyl, or, fluorine when $R^3$ is hydrogen or methyl and $R^4$ is hydrogen, or, chlorine when $R^3$ and $R^4$ are both hydrogen, chlorine or methyl, or, bromine when $R^3$ and $R^4$ are both hydrogen, provided that $R^2$, $R^3$ and $R^4$ are not all hydrogen, and provided that when one of $R^2$, $R^3$ or $R^4$ is methyl then at least one of the other two is not hydrogen and further provided that when any two of $R^2$, $R^3$ or $R^4$ are methyl then the other is not hydrogen;

X is

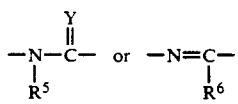

wherein $R^5$ is hydrogen, $C_{1-4}$ alkyl (optionally substituted by halogen or cyano), benzyl (wherein the phenyl moiety is optionally substituted by halogen, alkyl, haloalkyl, alkoxy, haloalkoxy, cyano or nitro), $C_{2-4}$ alkynyl or $C_{2-4}$ alkenyl; Y is oxygen or sulphur; $R^6$ is $C_{1-4}$ alkoxy or —NR$^9$ R$^{10}$; $R^9$ and $R^{10}$ are independently hydrogen, $C_{1-4}$ alkyl, aryl or aralkyl or $R^9$ and $R^{19}$ join to form a pyrrolidine, piperidine, morpholine, imidazole, pyrazole or 1,2,4-triazole ring.

3. A compound as claimed in claim 1 or 2 having the formula (I):

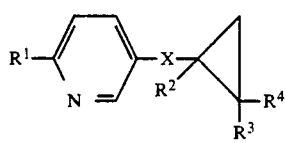

or a stereoisomer thereof, wherein $R^1$ is fluorine, chlorine or $C_{1-4}$ alkoxy; $R^3$ and $R^4$ are independently hydrogen, chlorine, fluorine or bromine; $R^2$ is hydrogen, or, fluorine, chlorine or bromine when $R^3$ and $R^4$ are both hydrogen, or $R^2$, $R^3$ and $R^4$ are all chlorine; provided that $R^2$, $R^3$, and $R^4$ are not all hydrogen;

X is

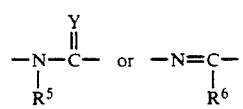

wherein $R^5$ is hydrogen, $C_{1-4}$ alkyl (optionally substituted by halogen or cyano), benzyl (wherein the phenyl moiety is optionally substituted by halogen, alkyl, haloalkyl, alkoxy, haloalkoxy, cyano or nitro), $C_{2-4}$ alkynyl or $C_{2-10}$ alkenyl; Y is oxygen or sulphur; $R^6$ is $C_{1-4}$ alkoxy or $-NR^9 R^{10}$; $R^9$ and $R^{10}$ are independently hydrogen, $C_{1-4}$ alkyl, aryl or aralkyl or $R^9$ and $R^{10}$ join to form a pyrrolidine, piperidine, morpholine, imidazole, pyrazole or 1,2,4-triazole ring.

4. A compound as claimed in claim 1 or 2 having the formula (IX):

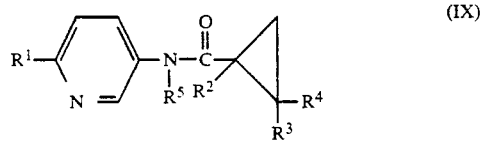

or a stereoisomer thereof, wherein $R^1$ is fluorine, chlorine or methoxy; $R^2$ and $R^4$ are both hydrogen and $R^3$ is fluorine, or $R^2$ is hydrogen and $R^3$ and $R^4$ are both fluorine, or $R^2$ is fluorine and $R^3$ and $R^4$ are both hydrogen; $R^5$ is hydrogen, $C_{1-4}$ alkyl (optionally substituted by cyano or fluorine), benzyl (wherein the phenyl moiety is optionally substituted by halogen, alkyl, haloalkyl, alkoxy, haloalkoxy, cyano or nitro), $C_{2-4}$ alkynyl or $C_{2-4}$ alkenyl.

5. A compound as claimed in claim 3 having the formula (IX):

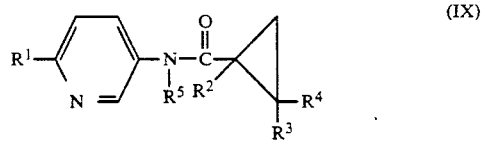

0 or a stereoisomer thereof, wherein $R^1$ is fluorine, chlorine or methoxy; $R^2$ and $R^4$ are both hydrogen and $R^3$ is fluorine, or $R^2$ is hydrogen and $R^3$ and $R^4$ are both fluorine, or $R^2$ is fluorine and $R^3$ and $R^4$ are both hydrogen; $R^5$ is hydrogen, $C_{1-4}$ alkyl (optionally substituted by cyano or fluorine), benzyl (wherein the phenyl moiety is optionally substituted by halogen, alkyl, haloalkyl, alkoxy, haloalkoxy, cyano or nitro), $C_{2-4}$ alkynyl or $C_{2-4}$ alkenyl.

6. A compound as claimed in claim 1 or 2 having the formula (IX):

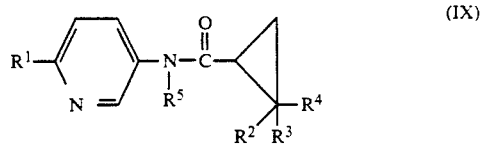

or a stereoisomer thereof, wherein $R^1$ is methoxy; $R^2$ and $R^4$ are both hydrogen and $R^3$ is fluorine, or $R^2$ is hydrogen and $R^3$ and $R^4$ are both fluorine, or $R^2$ is fluorine and $R^3$ and $R^4$ are both hydrogen; $R^5$ is hydrogen, $C_{1-2}$ alkyl (optionally substituted by cyano or fluorine), benzyl (wherein the phenyl moiety is optionally substituted by halogen, alkyl, haloalkyl, alkoxy, haloalkoxy, cyano or nitro), propargyl, allyl or but-2-ynyl.

7. A compound as claimed in claim 3 having the formula (IX):

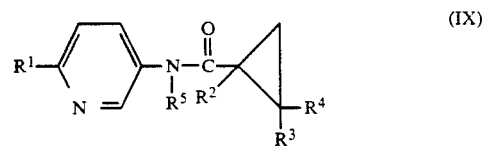

or a stereoisomer thereof, wherein $R^1$ is methoxy; $R^2$ and $R^4$ are both hydrogen and $R^3$ is fluorine, or $R^2$ is hydrogen and $R^3$ and $R^4$ are both fluorine, or $R^2$ is fluorine and $R^3$ and $R^4$ are both hydrogen; $R^5$ is hydrogen, $C_{1-2}$ alkyl (optionally substituted by cyano or fluorine), benzyl (wherein the phenyl moiety is optionally substituted by halogen, alkyl, haloalkyl, alkoxy, haloalkoxy, cyano or nitro), propargyl, allyl or but-2-ynyl.

8. A compound as claimed in claim 4 having the formula (IX):

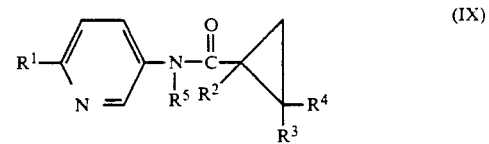

or a stereoisomer thereof, wherein $R^1$ is methoxy; $R^2$ and $R^4$ are both hydrogen and $R^3$ is fluorine, or $R^2$ is hydrogen and $R^3$ and $R^4$ are both fluorine, or $R^2$ is fluorine and $R^3$ and $R^4$ are both hydrogen; $R^5$ is hydrogen, $C_{1-2}$ alkyl (optionally substituted by cyano or fluorine), benzyl (wherein the phenyl moiety is optionally substituted by halogen, alkyl, haloalkyl, alkoxy, haloalkoxy, cyano or nitro), propargyl, allyl or but-2-yl.

9. A fungicidal composition comprising a fungicidally effective amount of a compound according to claim 1 and a fungicidally acceptable carrier or diluent therefor.

10. A method of combating fungi which comprises applying to plants, to the seeds of plants or to the locus of the plants or seeds, a compound according to claim 1 or a composition according to claim 9.

* * * * *